US006443730B2

(12) United States Patent
Davidson

(10) Patent No.: US 6,443,730 B2
(45) Date of Patent: Sep. 3, 2002

(54) BREAK-RESISTANT COMPOSITE ENDODONTIC INSTRUMENT

(76) Inventor: James A. Davidson, 7945 Farmington Blvd., Germantown, TN (US) 38138

(*) Notice: Subject to any disclaimer, the term of this patent is extended or adjusted under 35 U.S.C. 154(b) by 0 days.

(21) Appl. No.: 09/870,263

(22) Filed: May 30, 2001

Related U.S. Application Data

(60) Provisional application No. 60/208,612, filed on Jun. 1, 2000.

(51) Int. Cl.[7] .................................................. A61C 5/02
(52) U.S. Cl. .......................................................... 433/102
(58) Field of Search ................................. 433/102, 105, 433/166, 224

(56) References Cited

U.S. PATENT DOCUMENTS 5,273,558 A * 12/1993 Nelson et al. .............. 433/166
5,273,559 A * 12/1993 Hammar et al. ............ 433/166
6,183,253 B1 * 2/2001 Billet et al. ................. 433/224
6,267,597 B1 * 7/2001 Kim ........................... 433/224

* cited by examiner

Primary Examiner—Cary E. O'Connor
(74) Attorney, Agent, or Firm—Wyatt, Tarrant & Combs LLP

(57) ABSTRACT

A break-resistant composite comprising a plurality of fibers at least partially embedded in a polymer matrix forms a composite for making at least a portion of an endodonic instrument. At least a portion of the fibers are selected from a group consisting of partially twisted fibers and off-axis oriented fibers. The composite instrument can contain abrasive particulates to improve cutting and wear resistance for use in root canal procedures. The twisted fiber composite material allows for applied torque load response, improved flexibility within the root canal, and reduces or eliminates gross breakage of the instrument during use. The inventive composite can be molded or machined to make an endodnic instrument having certain desired diameters, tapers, helical recesses, and other design features.

20 Claims, 2 Drawing Sheets

BREAK-RESISTANT COMPOSITE ENDODONTIC INSTRUMENT

This application claims priority from Provisional application Ser. No. 60/208,612, filed Jun. 1, 2000.

FIELD OF THE INVENTION

The present invention is directed to a multi-fiber composite for making an endodontic reamer (dental file) for use in reaming, cleaning, and other preparation techniques in dental root canal procedures. More particularly, the multi-filament composite provides for a predominantly twisted or other off-axis oriented fiber construction (as a composite) at least partially embedded in a polymer matrix that can effectively transfer twisting (torque) loads, improve flexibility, and be highly resistant to complete (gross) breakage within the tooth canal.

BACKGROUND OF THE INVENTION

The tooth contains one or more circulatory and neural canal systems, terminating at each root. This canal is narrow, tapered and curved to varying degrees. The pulp tissue within the canal can become diseased. To avoid the need for extraction, the diseased tissue can be removed using endodontic files and reamers and the cleaned canal sealed. These endodontic cleaning instruments are tapered and have surface features (helical recesses, etc.) designed to remove the diseased pulp and other tissue within the canal via reciprocating or rotating motion. There are numerous patents that describe various flute, helix and other design features of root canal files and reamers including U.S. Pat. Nos. 5,735,689, 5,980,250, 4,299,571, 5,882,198, and 5,104,316 by McSpadden; U.S. Pat. Nos. 4,611,508 and 4,536,159 by Roane; and U.S. Pat. No. 4,538,989 by Apairo and Heath. Other design concepts include the use of tubular devices such as those described by Kronman and Goldman in U.S. Pat. No. 4,135,302 and by Gonser in U.S. Pat. No. 4,505,676.

Because of the narrow, curved nature of the root canal, repeated bending of the file induces high stress on current files made from stainless steel and other metals. As the modulus of elasticity (stiffness) of the metal increases, the stress on the file increases for a given curvature. The modulus of stainless steel, for example, is 30 msi. Although the inherent material strength can be quite high and often is above 200 ksi tensile, the recesses (helical) along the file length act as stress risers and can create a crack that propagates across the diameter of the file, leading to breakage. Breakage of the tip of a file creates a problem in removal of the imbedded broken piece. Typically a trephine-type device, as described Ruddle in U.S. Pat. No. 5,879,160, is needed to remove the broken pieces. This adds time and cost to the procedure and additional discomfort to the patient.

When the file or instrument is rotated within the canal, a repeated cyclic stress is imposed on the instrument. The number of rotations (or repeated stress events) of the instrument that occur until breakage is referred to as the fatigue life of the instrument. The issue of improved flexibility and longer fatigue life (rotations to breakage) of dental files has resulted in a more recent group of patents for lower-modulus titanium alloy files. These include U.S. Pat. No. 5,125,838 by Seigneurin and U.S. Pat. No. 5,984,679 by Farzin-Nia and Otsen. Titanium alloys have a much lower modulus (stiffness) than stainless steel and most have an elastic modulus of about 16 msi. Alloys such as super-elastic NiTi can accommodate exceptional displacements with a relatively lower imposed stress, and thus exhibit longer fatigue lives (*Nickel-Titanium Instruments*, Serene, et. al., 1995). The effective elastic modulus of NiTi alloys is in the range of 4–8 msi, half that of most standard titanium alloys. But NiTi alloys can cyclicly soften during repeated load cycles, which quickly change its initial mechanical characteristics (Ritchie and McKelvey, "Fatigue Crack Propogation in Nitinol.," JBMR, 47,301–308,1999). This aspect, in combination with typical file designs that generally have inherently sharp notches, results in a fatigue life governed primarily by fatigue crack propagation. Under these conditions, NiTi actually has a lower fatigue threshold than other titanium alloys. For example, the fatigue threshold for pure titanium (beta) is about 10 MPa-m$^{0.5}$ while that for NiTi is only about 2 MPa-m$^{0.5}$. Even 316 stainless steel has a fatigue threshold of about 6 MPa-m$^{0.5}$ (Ritchie and McKelvey, JBMR, 47, 1999). Thus, all metal files will have a finite life before eventually breaking. Table 1 below compares the number of revolutions to breakage, for a simulated canal root with a 90° bend, for stainless steel (K file) and NiTi (K file) files (*Nickel-Titanium Instruments*, Serene, et. al., 1995).

TABLE 1

Comparison revolutions to file breakage.

| Material (type) | Revolutions to breakage |
| --- | --- |
| Stainless Steel (No. 30, K file) | 38 |
| NiTi (No. 30, K file) | 125 |

Due to the high (super-elastic) flexibility of NiTi, it is difficult to machine or grind the flutes and other helical cutting features into a file or instrument. There are several patents that describe methods for grinding NiTi and other titanium alloys with more than 40 percent titanium. These patents are U.S. Pat. Nos. 5,464,362, 5,941,760, and 5,762, 541, by Heath and Mooneyhan and U.S. Pat. No. 5,984,679 by Farzin-Nia and Otsen.

There have been other approaches to reducing the tendency for breakage such as relocating the helical recesses (U.S. Pat. No. 5,106,298 by Heath and Mooneyhan), brazed metal composites (U.S. Pat. No. 5,927,912 by Mihai and Erpenbeck), and abi-metallic file with an inner metallic core to vary modulus (U.S. Pat. No. 5,380,200 by Heath and Berendt). Lower friction coatings have been proposed as well as design methods to reduce torsional force on the file. All of the above design and coating related approaches to reduce the tendency for file breakage are now well known in the art and are included within the scope of the present invention.

It should be noticed that all prior art relative to endodontic files relates only to solid metallic files. There is no prior art that describes the use of multi-fiber composite. It is an object therefore, of the present invention to provide a method of making an endodontic dental instrument, using fiber composite methods, that has low stiffness (good flexibility) and improved resistance to gross breakage.

SUMMARY OF THE INVENTION

The present invention is directed to an improved endodontic instrument incorporating any design feature, that can be tubular, and can have lubricating surface coatings. Unlike the currently used metal files, the inventive instrument is comprised of a plurality of fibers having a flexible polymer matrix. The polymer matrix can incorporate all fibers or only fibers near the outside diameter of the instrument. The fibers can be present as a core or present throughout the instrument. When present as a core, fiber-free polymer can comprise a portion of the surface and surface features. The polymer can have abrasive particles embedded within, at the surface or both, in order to improve cutting efficiency and to reduce wear of the polymer or polymer-fiber surface region.

The basic concept is similar to twisting a rope (the fiber) and freezing it in place (via the polymer matrix). The rope can be twisted and pushed but it can't "break." The inventive twisted fiber endodontic instrument is unique and distinguishable from that described in the prior art.

BRIEF DESCRIPTION OF THE DRAWINGS

The invention will become more apparent when the detailed description of the exemplary embodiments is considered in conjunction with the appended drawings in which.

DETAILED DESCRIPTION OF THE INVENTION

The subject invention is directed to a fiber-polymer composite endodontic instrument that is at least 30 percent partially pre-twisted fiber but can also include the use of a longitudinal fiber core. However, too many longitudinal fibers in the composite can result in too stiff a construction. Twisted fiber provides the most flexibility and is able to better accommodate applied torque, however a certain amount of strength is sacrificed. Preferably, the majority of the fibers are at least partially twisted so that the instrument has improved flexibility and can better respond to torque and axial compression loading imposed on the instrument during use A twisted fiber construction can be considered to be similar to fibers oriented at +/−45 degrees. Table 2 shows this relationship for carbon fiber reinforced polysulfone in which a dramatic reduction in stiffness occurs without the presence of longitudinal fibers. In this example, "Quasi" refers to a combination of longitudinal and +/−45 degree fibers.

TABLE 2

Tensile strength and modulus (stiffness) of various carbon fiber orientations in a polysulfone matrix (Davidson and Georgette, SME, 1987)

| Fiber orientation | Tensile strength (ksi) | Modulus (msi) |
|---|---|---|
| All longitudinal | 195 | 19 |
| +/− 45 degrees | 28 | 2 |
| Quasi (1 or 5 longitudinal and +/− 45°) | 72 | 7 |

The various combinations of pre-twisted fiber composite of the invention described above are known by those skilled in the art and fully incorporated in the subject invention.

Figure 2:
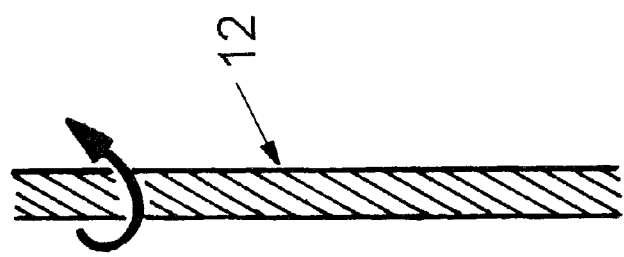
FIG. 2 is a schematic view of the fibers twisted and set in place within the matrix polymer after the molding.
Figure 1:
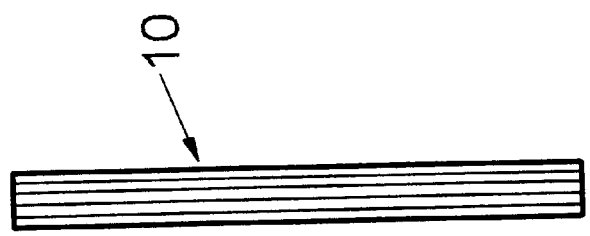
FIG. 1 is a schematic view of a group of longitudinally oriented fibers.

The preferred embodiment uses longitudinal fibers 10 (FIG. 1) as the starting material that are molded with a polymer matrix to form a pre-twisted-fiber core 12 (FIG. 2). Additional polymer 14 can be secondarily molded to the pre-twisted core 12. The pre-twisted core 12 can also contain abrasives 16 that can be embedded within the polymer or coated onto the outer surface 18 of the core 12. These particles can be diamond, such as the diamond coating described in U.S. Pat. No. 4,190,958 by Martin and Norris, metal filings or other hard abrasive particles such as alumina, carbides, nitrides, borides, silica, and the like. The hard particles can be incorporated into the polymer matrix, used as a coating in a final dip-coat or molding process, or a combination of any of the processes.

Figure 3:
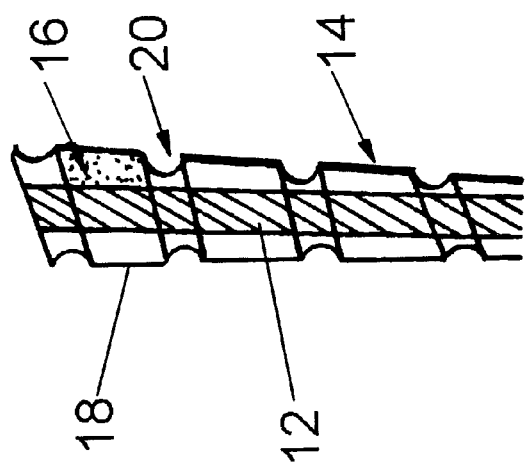
FIG. 3 is a schematic view of how additional polymer can be secondarily molded to a pre-twisted fiber core.
Figure 4:
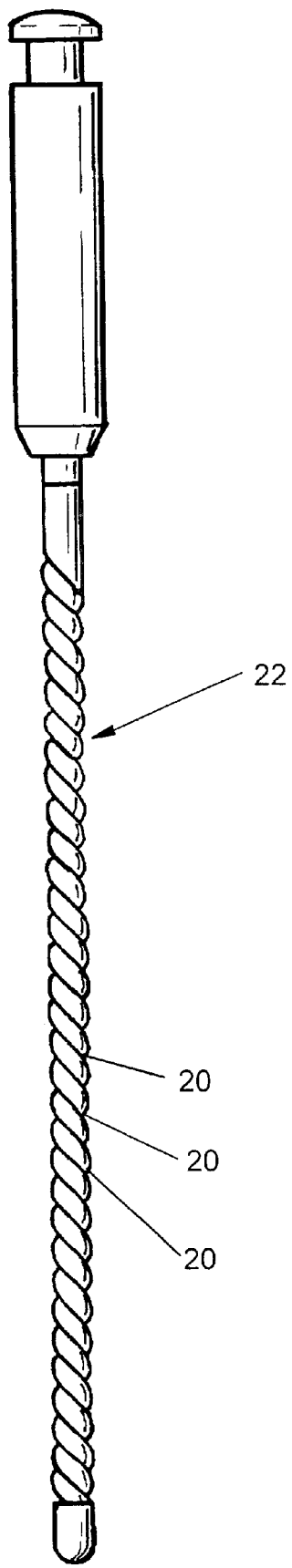
FIG. 4 is a plan side view of an illustrative example of an endodonitc instrument.

Helical recesses 20 can be machined or molded as desired. Preferably the majority of the inventive endodonic instrument is composed of the twisted fiber core 12 with a minimal amount of additional polymer molded or otherwise added to the surface of the twisted fiber core 12 (FIG. 3). The desired taper, recesses 20 and other design features can be molded or machined from this core 12 and polymer surface stock. Because of the increased flexability of the inventive file, straight longitudinal recesses can be used which will distort under the applied twisting load to form a helical shape during use. The polymer-rich surface 14 can be impregnated with abrasives 16, chopped fiber or both, or a molding or dip-coat process can be used to apply abrasive to the surface. Alternatively, both the matrix core 12 and surface regions 14 can contain abrasive particulates. Because the twisted core 12 serves as a twisted "rope" type construction, it is essentially immune to gross breakage as is found in the current metal instruments. Any small fragments that may detach from the composite instrument can be easily removed by using another instrument or a flushing-type instrument. FIG. 4 illustrates an example of an endodonic instrument 22.

In another embodiment, the entire instrument, including the taper, helical recesses and other design features, is formed entirely of the pre-twisted fiber-polymer composite material 12 in either an as-molded or as-machined (or ground) condition. The molding, grinding and machining processes used for various type composite materials are known by those skilled in the art and are included within the scope of the present invention.

Another embodiment can use the above described or similar opposing off-axis fiber orientation that results from a filament winding process. Although a solid shaft could be made in this fashion, this method would be particularly suited for the formation of a hollow tube type instrument. In an instrument having a tubular construct, flexibility can be further increased as well as providing for the use of flushing and suction options for use in root canal procedures. For a typical sized instrument (0.030 inch diameter), a tubular design will reduce the bending stiffness by 15 percent for a 0.006 inch wall and by 40 percent for a 0.003 inch wall, compared to a solid design of a given material.

Any type of fiber material can be used in the inventive construct, including glass, carbon, kevlar, silk, polyester, organic fiber such as cotton, hemp and the like, ceramic, metal, and other polymer fibers. The matrix can be comprised of any polymer, polymer alloy, or mixture, but it is preferred that polymers with relatively high melting temperatures be used so that the inventive device can tolerate steam autoclaving and potential frictional heating during use. Preferably, the polymer matrix will be resistant to damage from chemical sterilization methods as well. Polymers that meet these requirements include, but are not limited to, thermo-plastics such as keystones, including polyetherkeytones and this keystone family of polymers; polymides, including nylons and nylon-6; polyethersulfone; selected liquid crystal polymers; polyesters, including PET's and tough, high-temperature thermosets such as epoxy, methylmethacrylates, and phenolics.

One skilled in the art will readily appreciate that the present invention is well adapted to carry out the objects and obtain the ends and advantages mentioned as well as those inherent therein. The fiber reinforced polymer endodonic instrument described herein is presently representative of the preferred embodiments, are exemplary and are not intended as limitations on the scope of the invention. Changes therein and other uses will occur to those skilled in the art which are encompassed within the spirit of the invention and are defined by the scope of the claims.

What is claimed is:

1. A break-resistant endodontic reamer comprising a composite of a polymer matrix including a plurality of fibers at least partially embedded in the polymer matrix.

2. The break-resistant endodontic reamer of claim 1, wherein the polymer matrix includes a core having at least a portion of the fibers selected from a group consisting of partially twisted fibers and off-axis oriented fibers.

3. The break-resistant endodontic reamer of claim 2, wherein the core includes at least 30% of the fibers selected from a group consisting of partially twisted fibers and off-axis oriented fibers.

4. The break-resistant endodontic reamer of claim 2, wherein the composite includes regions of additional polymer.

5. The break-resistant endodontic reamer of claim 2, wherein the core surrounds a tapered hollow cylinder.

6. The break-resistant endodontic reamer of claim 5, wherein the reamer is adapted to include flusing and suction mechanisms.

7. The break-resistant endodontic reamer of claim 2, wherein the fiber orientation is off-axis in opposing directions, such as obtained from a filament winding process.

8. The break-resistant endodontic reamer of claim 1, wherein the polymer matrix includes an abrasive particulate material selected from the group consisting of an abrasive particulate material that is attached to the reamer, an abrasive particulate material that embedded within a surface of the reamer, and an abrasive particulate material that is attached to and embedded within a surface of the reamer.

9. The break-resistant endodontic reamer of claim 8, wherein at least a portion of the exterior surface of the reamer includes parallel longitudinal recesses.

10. The break-resistant endodontic reamer of claims 9, wherein the parallel recesses are helical.

11. The break-resistant endodontic reamer of claims 9, wherein the parallel recesses are machined.

12. The break-resistant endodontic reamer of claims 9, wherein the parallel recesses are molded.

13. The break-resistant endodontic reamer of claim 8, wherein the abrasive particulate material is selected from a group consisting of diamond, aluminum oxide, silicon dioxide, carbides, borides, nitrides and oxides.

14. The break-resistant endodontic reamer of claims 8, wherein the composite includes a core having at least a portion of the fibers selected from a group consisting of partially twisted fibers and off-axis oriented fibers.

15. The break-resistant endodontic reamer of claim 1, wherein the fiber material is selected from a group consisting of glass, carbon, kevlar, silk, polyester, organic fiber, ceramic, metal and polymer fibers.

16. The break-resistant endodontic reamer of claim 1, wherein the polymer matrix is selected from a group consisting of keystones, polyetherkeystone, polymides, nylon, nylon-6, acrylics, polymethylmethacralate; polyethersulfone, polyesters, PET, polyolifins, liquid crystal polymers, epoxy, and phenolics.

17. The break-resistant endodontic reamer of claim 1, wherein at least a portion of the polymer matrix includes chopped fiber.

18. The break-resistant endodontic reamer of claim 1, wherein entire endodontic reamer is made from the composite.

19. A break-resistant endodontic reamer comprising a plurality of fibers at least partially embedded in a polymer matrix forming a composite for making at least a portion of an endodontic reamer, wherein at least a portion of the fibers are selected from a group consisting of partially twisted fibers and off-axis oriented fibers.

20. A break-resistant endodontic reamer having a core comprising a plurality of fibers at least partially embedded in a polymer matrix, wherein at least 30% of the fibers are selected from a group consisting of partially twisted fibers and off-axis oriented fibers.

* * * * *